(12) United States Patent
Abe (10) Patent No.: US 10,143,382 B2
(45) Date of Patent: Dec. 4, 2018

(54) PHOTOACOUSTIC APPARATUS

(71) Applicant: CANON KABUSHIKI KAISHA, Tokyo (JP)

(72) Inventor: Hiroshi Abe, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 1010 days.

(21) Appl. No.: 14/502,040

(22) Filed: Sep. 30, 2014

(65) Prior Publication Data

US 2015/0099973 A1 Apr. 9, 2015

(30) Foreign Application Priority Data

Oct. 4, 2013 (JP) ................................. 2013-209624

(51) Int. Cl.
*A61B 5/00* (2006.01)
*G01N 21/17* (2006.01)

(52) U.S. Cl.
CPC ....... *A61B 5/0095* (2013.01); *G01N 21/1702* (2013.01); *G01N 2021/1706* (2013.01)

(58) Field of Classification Search
USPC ......................................................... 367/140
See application file for complete search history.

(56) References Cited

U.S. PATENT DOCUMENTS

| 2008/0194929 A1* | 8/2008 | Pesach | A61B 5/0066 600/310 |
| 2008/0252891 A1* | 10/2008 | Uber | G01N 21/1702 356/437 |
| 2009/0054763 A1* | 2/2009 | Wang | A61B 5/0059 600/425 |
| 2009/0312628 A1* | 12/2009 | Igarashi | A61B 5/0068 600/425 |
| 2011/0230761 A1* | 9/2011 | Peyman | A61K 41/0028 600/431 |
| 2011/0232385 A1* | 9/2011 | Nanaumi | A61B 5/0095 73/602 |
| 2011/0245652 A1* | 10/2011 | Oishi | A61B 5/0059 600/407 |
| 2012/0197113 A1* | 8/2012 | Courtney | A61B 8/12 600/427 |

(Continued)

OTHER PUBLICATIONS

"Photoacoustic Tomography: In Vivo Imaging From Organelles to Organs",Lihong V.Wang Song Hu,Science 335,1458 (2012)).

(Continued)

*Primary Examiner* — James R Hulka
(74) *Attorney, Agent, or Firm* — Canon USA, Inc. I.P. Division (57) ABSTRACT

A photoacoustic apparatus disclosed in the present specification includes: a light source configured to emit light; an acoustic wave transmission unit configured to transmit an acoustic wave to a specific area; a photoacoustic wave reception unit configured to receive a photoacoustic wave generated by a subject due to emission of the light, which is emitted from the light source, to the subject and configured to output a time-series photoacoustic signal; an echo reception unit configured to receive an echo generated due to reflection, in the subject, of the acoustic wave transmitted from the acoustic wave transmission unit and configured to output a time-series echo signal; and a processing unit configured to acquire, based on the time-series photoacoustic signal and the time-series echo signal, optical property information in which information a component corresponding to a reflected wave of the photoacoustic wave generated in the specific area is reduced.

19 Claims, 5 Drawing Sheets

(56) References Cited

U.S. PATENT DOCUMENTS

| | | | | |
|---|---|---|---|---|
| 2012/0253180 A1* | 10/2012 | Emelianov | A61B 8/0841 |
| | | | 600/424 |
| 2012/0259198 A1* | 10/2012 | Nagae | A61B 5/0095 |
| | | | 600/407 |
| 2013/0023752 A1* | 1/2013 | Khuri-Yakub | A61B 5/0095 |
| | | | 600/407 |
| 2013/0137960 A1* | 5/2013 | Lisogurski | A61B 5/0095 |
| | | | 600/407 |
| 2013/0197401 A1* | 8/2013 | Sato | A61N 7/00 |
| | | | 601/2 |
| 2013/0261427 A1* | 10/2013 | Oishi | A61B 5/0095 |
| | | | 600/407 |
| 2013/0274585 A1* | 10/2013 | Wanda | A61B 5/0095 |
| | | | 600/407 |
| 2014/0005537 A1* | 1/2014 | Asami | A61B 5/0095 |
| | | | 600/431 |
| 2014/0114172 A1* | 4/2014 | Abe | A61B 5/0095 |
| | | | 600/407 |
| 2015/0007659 A1* | 1/2015 | Nanaumi | A61B 5/0095 |
| | | | 73/602 |
| 2015/0098305 A1* | 4/2015 | Abe | A61B 5/7235 |
| | | | 367/87 |
| 2015/0351639 A1* | 12/2015 | Abe | A61B 8/4416 |
| | | | 600/407 |

OTHER PUBLICATIONS

"Acoustic radiation force impulse imaging of myocardial radio-frequency ablation: initial in vivo results", Fahey et al., IEEE Transactions on Ultrasonics, Ferroelectrics and Frequency Control, vol. 52, Issue 4, Apr. 2005 pp. 631-641.

* cited by examiner

PHOTOACOUSTIC APPARATUS

BACKGROUND OF THE INVENTION

Field of the Invention

The present invention relates to a photoacoustic apparatus to acquire optical property information by using a photoacoustic wave.

Description of the Related Art

A study of an optical imaging apparatus to image information inside a subject, which information is acquired by emitting light from a light source such as a laser to the subject such as a living body and acquired based on the incident light, has been actively done in a medical field. As one kind of the optical imaging technique, there is photoacoustic imaging (PAI). In the photoacoustic imaging, pulsed light generated in a light source is emitted to a subject and an acoustic wave (typically, ultrasonic wave) generated in a subject tissue which absorbs energy of the pulsed light propagated and diffused in the subject is received. Based on the received signal, imaging of information of the subject is reconstructed.

That is, by using a difference between absorptance of optical energy in an object region such as a tumor and that in other tissues, an elastic wave (photoacoustic wave) generated when a region to be inspected absorbs the emitted optical energy and instantaneously expands is received by a probe. By performing mathematical analysis processing on this received signal, optical property information inside the subject, specifically, initial sound pressure distribution, optical energy absorption density distribution, absorption coefficient distribution, or the like can be acquired.

These pieces of information can also be used, for example, for a quantitative measurement of a specific substance inside the subject such as oxygen saturation in blood. Recently, by using the photoacoustic imaging, a preclinical study to image a blood vessel image of a small animal or a clinical study to apply this principle to a diagnosis of a breast cancer or the like has been actively done ("Photoacoustic Tomography: In Vivo Imaging From Organelles to Organs", Lihong V. Wang Song Hu, Science 335, 1458 (2012)). In the photoacoustic imaging, generally, it is desired to image optical property distribution of an optical absorber inside the subject.

SUMMARY OF THE INVENTION

A photoacoustic apparatus disclosed in the present specification includes: a light source configured to emit light; an acoustic wave transmission unit configured to transmit an acoustic wave to a specific area; a photoacoustic wave reception unit configured to receive a photoacoustic wave generated by a subject due to emission of the light, which is emitted from the light source, to the subject and configured to output a time-series photoacoustic signal; an echo reception unit configured to receive an echo generated due to reflection, in the subject, of the acoustic wave transmitted from the acoustic wave transmission unit and configured to output a time-series echo signal; and a processing unit configured to acquire, based on the time-series photoacoustic signal and the time-series echo signal, optical property information of the subject in which information a component corresponding to a reflected wave of the photoacoustic wave generated in the specific area is reduced.

Further features of the present invention will become apparent from the following description of exemplary embodiments (with reference to the attached drawings).

DESCRIPTION OF THE EMBODIMENTS

A photoacoustic wave generated in an optical absorber is transmitted and propagated isotropically with a shape of the optical absorber as an origin. Then, a probe receives not only a photoacoustic wave directly propagated thereto from the optical absorber but also a reflected wave generated due to reflection of the photoacoustic wave generated in the optical absorber. Since the reflected wave is not propagated to the probe directly and takes different time of flight, reconstructed image does not depict a true optical absorber's figure. Then, decrease in quantitativity of optical property information acquired from a received signal including a component corresponding to this reflected wave is caused.

The photoacoustic apparatus disclosed in the present specification uses a received signal of an echo of an acoustic wave transmitted to a specific area and acquires optical property information from which a component corresponding to a reflected wave of a photoacoustic wave generated in the specific area is reduced. Specifically, since intensity of a photoacoustic wave generated in a part to which light is directly emitted (such as skin on surface of subject, acoustic lens arranged on surface of probe, or the like) is high, intensity of a reflected wave of the photoacoustic wave also becomes high. Thus, quantitativity of acquired optical property information is greatly decreased due to such a reflected wave. In each embodiment, a case where a component corresponding to a reflected wave of a photoacoustic wave generated on a surface of a subject is reduced based on a received signal of an echo will be described. That is, in each embodiment, a surface of a subject to which light is emitted will be described as a source of a reflected wave. In the following, an effect in each embodiment will be described.

A waveform of a reflected wave generated due to reflection, by a reflector inside the subject, of a photoacoustic wave generated on a surface of a subject and a waveform of an echo generated due to reflection of a transmitted acoustic wave by the same reflector become similar shapes. Thus, a received signal of the reflected wave of the photoacoustic wave and a received signal of the echo become similar signals.

Thus, by acquiring a difference signal between a received signal of a photoacoustic wave and a received signal of an echo, a photoacoustic apparatus according to a first embodiment can reduce a component corresponding to a reflected wave of the photoacoustic wave.

Incidentally, distribution of an initial sound pressure of when a photoacoustic wave is generated can be acquired from a received signal of the photoacoustic wave. On the other hand, similarly to the initial sound pressure distribution, sound pressure distribution of an echo of when the echo is generated can be acquired from a received signal of the echo. Then, components respectively corresponding to a reflected wave of the photoacoustic wave and an echo, which are by the same reflector, respectively appear at the same position in the initial sound pressure distribution and the echo sound pressure distribution.

Thus, by acquiring difference distribution between initial sound pressure distribution acquired from a received signal of a photoacoustic wave and echo sound pressure distribution acquired from a received signal of an echo, a photoacoustic apparatus according to a second embodiment can reduce a component corresponding to a reflected wave of the photoacoustic wave.

As described, according to a photoacoustic apparatus disclosed in the present specification, a component corresponding to a reflected wave of a photoacoustic wave can be reduced. Thus, according to the photoacoustic apparatus disclosed in the present specification, decrease in quantitativity of optical property information due to a component corresponding to a reflected wave of a photoacoustic wave can be controlled.

Note that as the optical property information, there are initial sound pressure distribution of a photoacoustic wave, optical energy absorption density distribution, absorption coefficient distribution, concentration distribution of a substance included in a subject, and the like. Here, a concentration of a substance is, for example, oxygen saturation, an oxyhemoglobin concentration, a deoxyhemoglobin concentration, or a total hemoglobin concentration.

Also, a reflected wave in the present specification includes an acoustic wave generated by scattering.

In the following, embodiments of a photoacoustic apparatus according to the present invention will be described in detail with reference to the attached drawings. However, the scope of the invention is not limited to the illustrated examples.

First Embodiment

Figure 1:
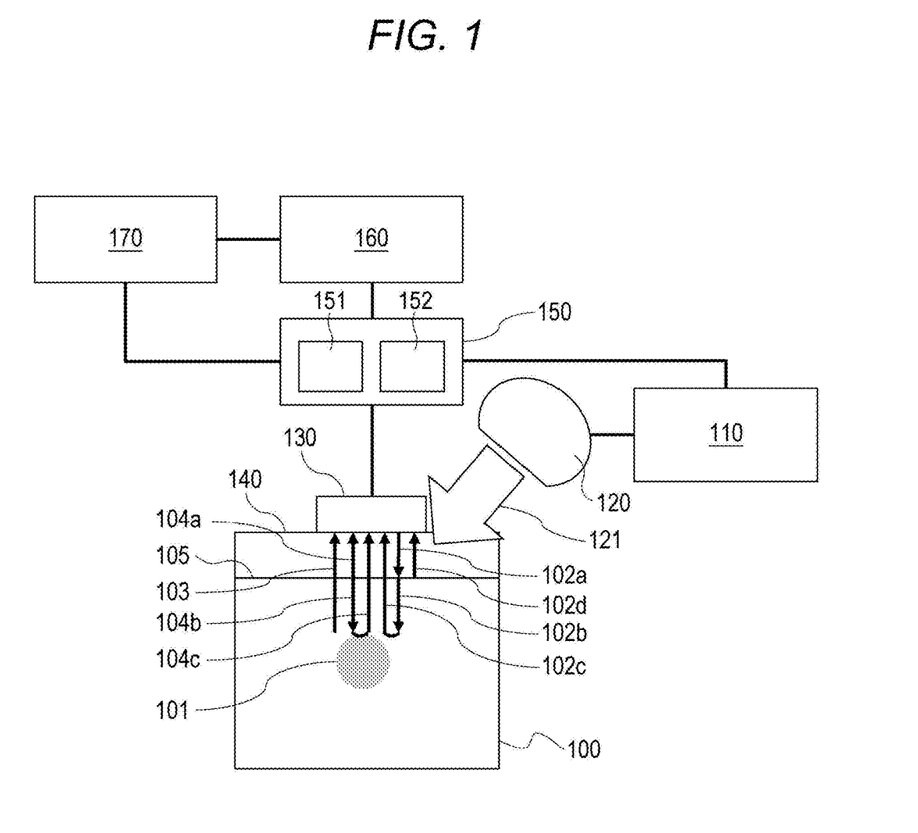
FIG. 1 is a schematic view illustrating a photoacoustic apparatus according to a first embodiment.

A photoacoustic apparatus according to the present embodiment will be described with reference to FIG. 1. FIG. 1 is a view schematically illustrating the photoacoustic apparatus according to the present embodiment. By acquiring a difference signal between a received signal of a photoacoustic wave and a received signal of an echo of a transmitted acoustic wave, the photoacoustic apparatus according to the present embodiment reduces a component corresponding to a reflected wave of the photoacoustic wave.

In the following, a received signal of a photoacoustic wave is also referred to as a "photoacoustic signal" and a received signal of an echo of a transmitted acoustic wave is also referred to as an "echo signal".

The photoacoustic apparatus according to the present embodiment includes a light source 110, an optical system 120, a transducer array 130, a computer 150 as a processing unit, a display unit 160, and an input unit 170. Note that the transducer array 130 includes a function as an acoustic wave transmission unit configured to transmit an acoustic wave to a subject 100. Also, the transducer array 130 includes functions as a photoacoustic wave reception unit configured to receive a photoacoustic wave and an echo reception unit configured to receive an echo.

Figure 2:
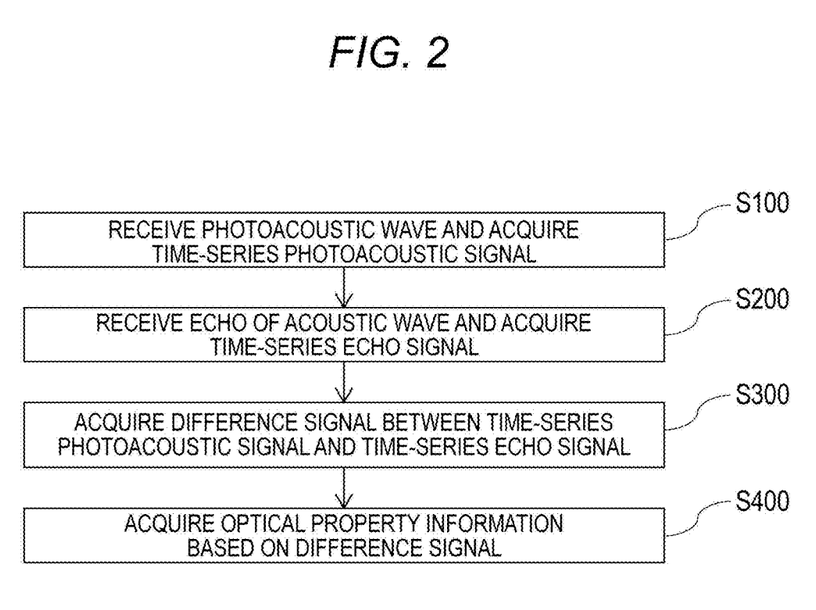
FIG. 2 is a flowchart illustrating an operation flow of the photoacoustic apparatus according to the first embodiment.

Next, an operation of the photoacoustic apparatus according to the present embodiment will be described with reference to FIG. 2. Note that the computer 150 controls an operation of each configuration of the photoacoustic apparatus.

(S100: Process for Receiving Photoacoustic Wave and Acquiring Time-Series Photoacoustic Signal)

First, the light source 110 generates pulsed light 121. The pulsed light 121 is emitted to the subject 100 through the optical system 120. Then, the pulsed light 121 is absorbed by an optical absorber 101 placed inside the subject 100. The optical absorber 101 which has absorbed the pulsed light 121 expands instantaneously, and thus, a photoacoustic wave 103 is generated. On the other hand, the pulsed light 121 is absorbed also on a surface 105 of the subject 100 and a photoacoustic wave is generated. The photoacoustic wave generated on the surface 105 of the subject 100 is classified broadly into a photoacoustic wave 104a generated in a direction of the transducer array 130 and a photoacoustic wave 104b generated in an opposite direction of the transducer array 130. The photoacoustic wave 104b is propagated in the subject 100 and reflected by the optical absorber 101, and thus, a reflected wave 104c is generated. In the present embodiment, each of the photoacoustic waves 104a and 104b generated on the surface 105 of the subject 100 is a photoacoustic wave generated in a part to which the pulsed light 121 is directly emitted.

The transducer array 130 receives a photoacoustic wave including the photoacoustic wave 104a and the reflected wave 104c and converts the received photoacoustic wave into a time-series photoacoustic signal S1 ($t$). The computer 150 performs processing of amplification and A/D conversion on the time-series photoacoustic signal S1 ($t$) output from the transducer array 130 and houses the processed signal into a storage unit 151 in the computer 150. It is assumed that t indicates time and t=0 is a time point at which a light source 110 generates the pulsed light 121. That is, the computer 150 performs control to start acquiring a photoacoustic signal at the time point at which the light source 110 generates the pulsed light 121. For example, by controlling driving of the transducer array 130 or housing, into a memory, of the photoacoustic signal output from the transducer array 130, the computer 150 can control acquisition of the photoacoustic signal.

Figure 3A:
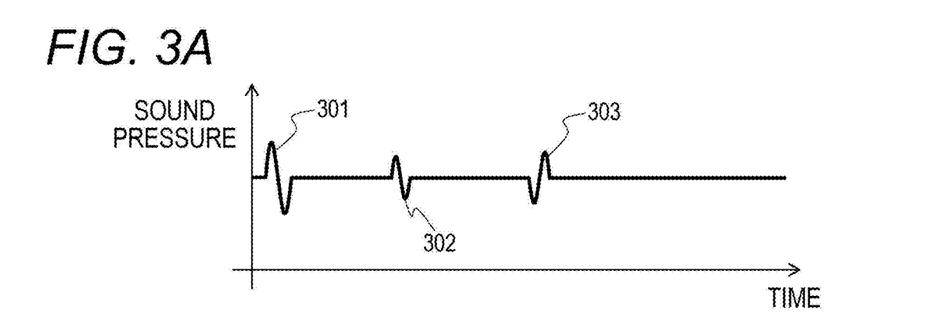
FIGS. 3A to 3C are views illustrating various signals which can be acquired in the first embodiment.

Here, the time-series photoacoustic signal S1 ($t$) will be described. FIG. 3A is a view illustrating the time-series photoacoustic signal S1 ($t$) acquired by a specific transducer.

An interface signal 301 in the time-series photoacoustic signal S1 ($t$) is a received signal of the photoacoustic wave 104a generated on the surface 105 of the subject 100. Also, an absorber signal 302 is a received signal of the photoacoustic wave 103 generated in the optical absorber 101. Also, a reflected signal 303 is a received signal of the reflected wave 104c generated due to reflection, by the optical absorber 101, of the photoacoustic wave 104b generated on the surface 105 of the subject 100. That is, the reflected signal 303 is a component corresponding to a reflected wave in the time-series photoacoustic signal S1 ($t$).

(S200: Process for Receiving Echo of Transmitted Acoustic Wave and Acquiring Time-Series Echo Signal)

In the present process, first, the transducer array 130 transmits an acoustic wave 102a to the subject 100. The acoustic wave 102a is propagated in an acoustic matching material 140 and reaches the surface 105 of the subject 100. A part of the acoustic wave 102a is reflected by the surface 105 of the subject 100 and becomes a component of an echo 102d and a part of the acoustic wave 102a is transmitted and becomes a component of an acoustic wave 102b. The acoustic wave 102b is reflected by the optical absorber 101 as a reflector and an echo 102c is generated.

The transducer array 130 receives the echoes 102c and 102d and converts the received echoes into a time-series echo signal S2 (t). Then, the computer 150 performs processing of amplification and A/D conversion on the time-series echo signal S2 (t) output from the transducer array 130 and houses the processed signal into the storage unit 151 in the computer 150. In the time-series echo signal S2 (t), it is assumed that t=0 is a time point at which the transducer array 130 transmits the acoustic wave 102a.

Figure 3B:
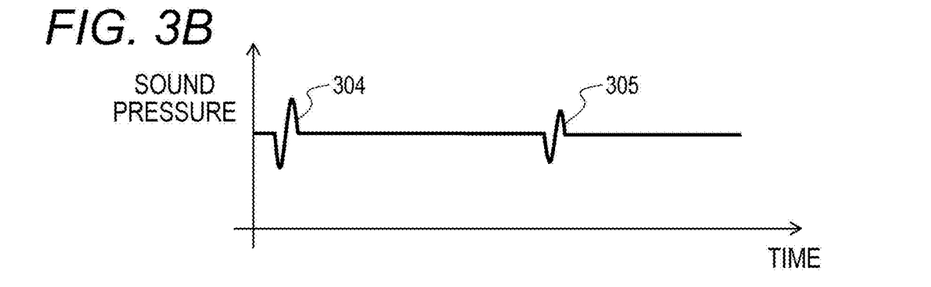

Here, the time-series echo signal S2 (t) will be described. FIG. 3B is a view illustrating the time-series echo signal S2 (t) acquired by a specific transducer. A reflected signal 304 in the time-series echo signal S2 (t) is a received signal of the echo 102d reflected by the surface 105 of the subject 100. A reflected signal 305 is a received signal of the echo 102c generated due to reflection, by the optical absorber 101, of the acoustic wave 102b transmitted through the surface 105 of the subject 100.

<Transmission Waveform>

To make the echo 102c reproduce the reflected wave 104c of the photoacoustic wave 104b, a transmission waveform of the transducer array 130 is preferably controlled in such a manner that a waveform of the acoustic wave 102b and a waveform of the photoacoustic wave 104b become similar to each other. In the following, an example of a method for determining a transmission waveform will be described. Note that a method is not limited to the following method, as long as a transmission waveform, with which the waveform of the acoustic wave 102b and the waveform of the photoacoustic wave 104b become similar to each other, can be determined.

First, the computer 150 estimates a waveform of the photoacoustic wave 104b based on a size or a shape of the surface 105 (source of reflected wave) of the subject 100. In the photoacoustic wave, a waveform having a different frequency characteristic is generated depending on a shape of a substance. As a general solution, it is known that when a shape of the optical absorber is a slab shape, the waveform becomes a waveform protruded upward, and in a case of a spherical shape, the waveform becomes an N-shaped waveform. Thus, from a shape of the source of a reflected wave, a waveform of the photoacoustic wave generated in the source of a reflected wave can be estimated.

Subsequently, the computer 150 can calculate a waveform to be transmitted from the transducer array 130 by a photoacoustic wave equation in such a manner that a waveform of the acoustic wave 102b and a waveform of the photoacoustic wave 104b become similar to each other. Note that according to a waveform to be reproduced, the computer 150 can arbitrarily calculate a waveform to be transmitted by the photoacoustic wave equation including the decay factor or transducer's response function.

Also, the computer 150 may determine a transmission waveform of the transducer array 130 based on the time-series photoacoustic signal S1 (t) acquired in S100.

The computer 150 can extract a received signal of the photoacoustic wave 104a from the time-series photoacoustic signal S1 (t) and can calculate a transmission waveform to reproduce a waveform of the photoacoustic wave 104b at generation from the received signal of the photoacoustic wave 104a. Since a photoacoustic wave is isotropically generated, the photoacoustic wave 104a and the photoacoustic wave 104b have similar waveforms. Thus, a transmission waveform to reproduce the photoacoustic wave 104b at the generation can be calculated from the received signal of the photoacoustic wave 104a. Here, it is preferable that the computer 150 calculates a transmission waveform in consideration of a frequency characteristic of a transducer, frequency attenuation during propagation of an acoustic wave, a transducer response, or the like.

Also, based on amplitude, a pulse width, or the like of the received signal of the photoacoustic wave 104a, the computer 150 may select, from a plurality of transmission waveforms stored in the storage unit 151 in the computer 150, a transmission waveform to reproduce a waveform of the photoacoustic wave 104b at the generation.

Note that by a method described in the following, a received signal of the photoacoustic wave 104a can be extracted from the time-series photoacoustic signal S1 (t) acquired in S100. However, a method is not limited to the following method as long as a received signal of an object photoacoustic wave can be extracted.

Since the surface 105 of the subject 100 is a part to which light is directly emitted, amplitude of the photoacoustic wave 104a becomes relatively large. Thus, the computer 150 can extract, from the time-series photoacoustic signal S1 (t), a waveform having the largest amplitude as a received signal of the photoacoustic wave 104a.

Also, since the surface 105 of the subject 100 is close to the transducer array 130, the photoacoustic wave 104a reaches the transducer array 130 prior to the other photoacoustic waves. Thus, the computer 150 can extract, as a received signal of the photoacoustic wave 104a, a waveform which has amplitude equal to or larger than a threshold and is output from the time-series photoacoustic signal S1 (t) in the beginning.

Also, the time-series photoacoustic signal S1 (t) may be displayed on the display unit 160 and an arbitrary waveform may be selected, as a received signal of the photoacoustic wave 104a, with the input unit 170 by a user.

Also, initial sound pressure distribution P1 (r) acquired from the time-series photoacoustic signal S1 (t) by a method which will be described later may be displayed on the display unit 160 and an arbitrary position of the initial sound pressure distribution P1 (r) may be specified with the input unit 170 by a user. Accordingly, a received signal of the photoacoustic wave 104a can be extracted. For example, a plurality of photoacoustic signals, which is used to reconstruct an initial sound pressure at a specified position, can be averaged and selected as a received signal of the photoacoustic wave 104a. Also, among the plurality of photoacoustic signals, which is used to reconstruct an initial sound pressure at a specified position, a waveform of an arbitrary photoacoustic signal can be selected as a received signal of the photoacoustic wave 104a. Note that it is preferable that a photoacoustic signal output from a transducer which anticipates a specified position in a direction of high directionality is selected as a received signal of the photoacoustic wave 104a.

Also, the transducer 130 may form the acoustic wave 102b by forming a great number of virtual point sound sources along a shape of the source of a reflected wave by using a known method such as an acoustic radiation force impulse (ARFI) described in "Acoustic radiation force impulse imaging of myocardial radio-frequency ablation: initial in vivo results", Fahey et al., IEEE Transactions on Ultrasonics, Ferroelectrics and Frequency Control, Volume 52, Issue 4, April 2005 Page(s): 631-641. Here, based on shape information acquired by a shape acquisition unit, the computer 150 can determine positions to form the virtual point sound sources. The computer 150 can control a transmission waveform of the transducer array 130 in such a manner that the virtual point sound sources can be formed in determined positions.

<Propagation Path>

Note that as a matter of convenience, in FIG. 1, the acoustic wave 102b and the echo 102c, and the photoacoustic wave 104b and the reflected wave 104c are illustrated in different propagation paths. However, the acoustic waves preferably include similar propagation paths in such a manner that a waveform of the reflected wave 104c and a waveform of the echo 102c become similar to each other. Thus, the computer preferably controls arrangement of the optical system 120 and the transducer array 130 and a transmission direction of the acoustic wave 102a in such a manner that a position to which the pulsed light 121 is emitted and a position to which the acoustic wave 102a is transmitted become similar to each other.

Also, a deviation between a position of the transducer array 130 to receive a photoacoustic wave in S100 and a position of the transducer array 130 to receive an echo in S200 is preferably small. By making the transducer array 130 placed in such a manner, the reflected wave 104c and the echo 102c are output in similar received signals.

(S300: Process for Acquiring Difference Signal Between Time-Series Photoacoustic Signal and Time-Series Echo Signal)

In this process, a difference signal S3 ($t$) between the time-series photoacoustic signal S1 ($t$) acquired in S100 and the time-series echo signal S2 ($t$) acquired in S200 is acquired. For example, by subtracting the time-series echo signal S2 ($t$) from the time-series photoacoustic signal S1 ($t$), the difference signal S3 ($t$) illustrated in FIG. 3C is acquired.

Figure 3C:
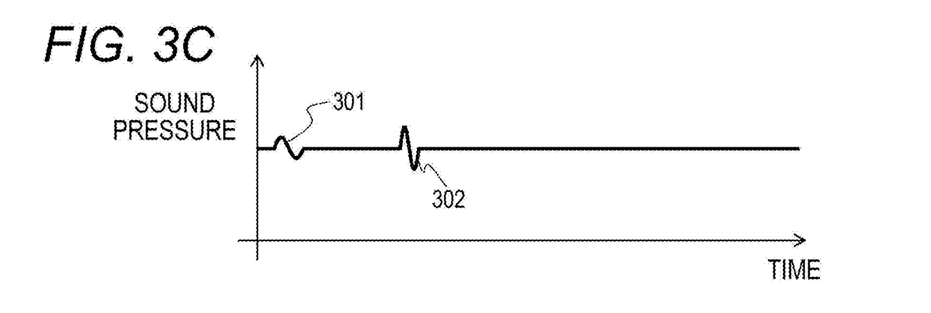

According to FIG. 3C, it can be understood that the reflected signal 303 in the time-series photoacoustic signal S1 ($t$) is reduced as a result of the subtraction of the time-series echo signal S2 ($t$) from the time-series photoacoustic signal S1 ($t$). On the other hand, an absorber signal 302 due to the photoacoustic wave 103 generated in the optical absorber 101 is also reproduced by the difference signal S3 ($t$). Thus, by acquiring the difference signal S3 ($t$) between the time-series photoacoustic signal S1 ($t$) and the time-series echo signal S2 ($t$), the reflected signal 303 (component corresponding to reflected wave of photoacoustic wave) can be selectively reduced.

Note that as a method for performing differential processing, subtraction in signals of time base data has been performed. However, any method can be used as long as a difference between signal components at predetermined reception time can be acquired. For example, a difference signal may be acquired by the following manner. That is, by using a Fourier space, a window function of a time interval, a center of which is a position (time) of a waveform to be subtracted, is multiplied by S1 ($t$) and S2 ($t$) and is Fourier-transformed, and then, the same frequency spectrum component is subtracted and inverse Fourier transform is performed. When a wavelet space is used as a base space, between the signals which are wavelet-transformed S1 ($t$) and S2 ($t$), a signal coefficient which is in the same time interval is subtracted and inversely transformed, and thus, a difference signal can be acquired.

<Deviation Correction of Reception Time>

In the present embodiment, it is assumed that in the time-series photoacoustic signal S1 ($t$), a time point at which the pulsed light 121 is emitted is t=0 (reference) and in the time-series echo signal S2 ($t$), a time point at which the acoustic wave 102a is transmitted is t=0 (reference). However, practically, a period of time from the time point at which the acoustic wave 102a is transmitted to the time point at which the acoustic wave 102a reaches the surface 105 of the subject 100 does not become zero. In this case, reception time of the reflected signal 303 (received signal of reflected wave 104c) in the time-series photoacoustic signal S1 ($t$) and reception time of the reflected signal 305 (received signal of echo 102c) in the time-series echo signal S2 ($t$) are not identical. Thus, a correction to deviate a reference of the reception time of the time-series photoacoustic signal S1 ($t$) or the time-series echo signal S2 ($t$) may be performed in such a manner that a difference in the reception time of the reflected signals becomes small. That is, to make a difference in the reception time of the echo small, a difference signal may be acquired after the time-series photoacoustic signal S1 ($t$) or the time-series echo signal S2 ($t$) is corrected. Also, correction is preferably performed in such a manner that the reception time of the reflected signals becomes identical.

Here, the computer 150 can calculate time of flight of an acoustic wave from arrangement of the transducer array 130 and the subject 100 and can calculate deviation time of a reference.

Also, the computer 150 may determine a signal, which is similar to the reflected signal 303, from the time-series echo signal S2 ($t$) and may deviate a reference in such a manner that a difference in the reception time of these signals becomes small. Alternatively, the computer 150 may determine a signal, which is similar to the reflected signal 305, from the time-series photoacoustic signal S1 ($t$) and may deviate a reference in such a manner that a difference in the reception time of these signals becomes small. Here, the computer 150 can determine a similar signal by means to use a cross-correlation such as template matching.

Note that as a method for determining the reflected signal 303 from the time-series photoacoustic signal S1 ($t$), a signal similar to an antiphase waveform of the interface signal 301 is extracted. Also, by selecting the signal similar to the antiphase waveform of the interface signal 301 from the time-series echo signal S2 ($t$), it is also possible to extract the reflected signal 305.

Note that when deviation time of a reference is in a degree which can be ignored in reduction of a component corresponding to a reflected wave of a time-series photoacoustic signal, it is not necessary to deviate the reference.

Also, the time point at which the acoustic wave 102a reaches the surface 105 of the subject 100 may be set as t=0 in the time-series echo signal S2 ($t$). That is, the computer 150 may perform control in such a manner that acquisition of an echo signal is started at the time point at which the acoustic wave 102a reaches the surface 105 of the subject 100. For example, the computer 150 can control the acquisition of an echo signal by controlling driving of the transducer array 130 or housing, into a memory, of an echo signal output from the transducer array 130.

Also, the computer 150 may delete, from the time-series echo signal S2 ($t$), an echo signal acquired before the acoustic wave 102a reaches the surface 105 of the subject 100.

By the above method, it is possible to make the reception time of the reflected waves identical.

<Weighting>

Incidentally, there is a case where intensity of the photoacoustic wave 104a generated on the surface 105 of the subject 100 and that of the acoustic wave 103a transmitted from the transducer array 130 are different from each other. In such a case, it is preferable that a difference between the time-series photoacoustic signal and the time-series echo signal is calculated and the difference signal S3 (t) is acquired after weighting is performed on the time-series photoacoustic signal S1 (t) or the time-series echo signal S2 (t). By performing such weighting processing, a component corresponding to a reflected wave in the time-series photoacoustic signal S1 (t) can be reduced further greatly.

The following equation is an equation expressing an example of the described weighting processing.

$$S3(t)=S1(t)-a \times S2(t) \quad (1)$$

Here, a is a weighting coefficient. The weighting coefficient a is a value which reduces a difference between an amplitude value of a photoacoustic signal corresponding to a reflected wave generated due to reflection of a photoacoustic wave by a reflector and an amplitude value of an echo signal corresponding to an echo generated due to reflection of the transmitted acoustic wave by the same source of a reflected wave. The weighting coefficient a can be arbitrarily set by a user or a computer.

Signals having a high correlation with the time-series photoacoustic signal S1 (t) and the time-series echo signal S2 (t) are likely to be received signals of the reflected waves reflected by a specific reflector. Thus, it is preferable that the computer 150 sets the weighting coefficient a with which a difference in amplitude of the signals having a high correlation with the time-series photoacoustic signal S1 (t) and the time-series echo signal S2 (t) becomes small. Also, the computer 150 preferably sets the weighting coefficient a with which amplitude of the signals having a high correlation becomes identical.

In an example of the weighting expressed in the equation 1, the weighting is performed by multiplying the time-series echo signal S2 (t) by a weighting coefficient. Note that in the present embodiment, the weighting may be performed by multiplying the time-series photoacoustic signal S1 (t) by a weighting coefficient or the weighting may be performed by multiplying both of the time-series photoacoustic signal S1 (t) and time-series echo signal S2 (t) by a weighting coefficient. However, to maintain quantitativity of optical property information which can be acquired from the time-series photoacoustic signal S1 (t), only the time-series echo signal S2 (t) is preferably multiplied by a weighting coefficient.

Also, it is preferable that the weighting processing is performed after the above-described correction of a reference is performed in order to make it easier to compare amplitude of the signals.

Also, to selectively reduce a component corresponding to a reflected wave from the time-series photoacoustic signal S1 (t), a time-series echo signal on which envelope detection is performed may be used as a mask of the time-series photoacoustic signal S1 (t). That is, the computer 150 may acquire a difference signal between the time-series photoacoustic signal S1 (t) masked by the time-series echo signal on which the envelope detection is performed and the time-series echo signal S2 (t). Also, a binarization signal, in which a case where an amplitude value of the echo signal on which the envelope detection is performed is equal to or higher than a predetermined threshold is one and the rest of the cases is zero, may be used as a mask of the time-series photoacoustic signal S1 (t).

Incidentally, in the present embodiment, the interface signal 301 is reduced by acquiring a difference signal with the reference signal 304. Note that by replacing the reduced interface signal with the interface signal 301 stored in the storage unit 151, the computer 150 can restore the interface signal 301. Also, by adding an antiphase signal of the reflected signal 304 to the reduced interface signal, the computer 150 can restore the interface signal 301.

(S400: Process for Acquiring Optical Property Information from Difference Signal S3 (t))

The computer 150 acquires optical property information based on the difference signal S3 (t) acquired in S300. As described, since the difference signal S3 (t) is a signal in which a component corresponding to a reflected wave of the photoacoustic wave is reduced, a component corresponding to the reflected wave of the photoacoustic wave is also reduced in the optical property information acquired based on the difference signal S3 (t).

In the present process, the computer 150 can perform reconstruction processing by using the difference signal S3 (t) and can form initial sound pressure distribution as the optical property information. As reconstruction algorithm, for example, back projection in a time domain or a Fourier domain, delay-and-sum (DAS), or the like generally used in tomography technique is used. Also, when it is possible to spend a long period of time on reconstruction, an image reconstruction method such as an inverse problem analysis method by iteration processing can also be used. Note that when the time-series photoacoustic signal S1 (t) is acquired by serially scanning a transducer array focused in S100, high dimensional initial sound pressure distribution can be formed without the reconstruction. In this case, it is not necessary for the computer 150 to perform the reconstruction processing.

Note that by acquiring light quantity distribution, in the subject 100, of the light emitted to the subject 100 in S100 and correcting the initial sound pressure distribution with the light quantity distribution, the computer 150 can acquire absorption coefficient distribution as the optical property information. Moreover, the computer 150 can acquire, by using light of a plurality of wavelengths, absorption coefficient distribution corresponding to each of the wavelengths. By using the absorption coefficient distribution, the computer 150 can acquire, as the optical property information, a concentration of a substance included in the subject 100.

Subsequently, the computer 150 acquires image data to be displayed on the display unit 160 based on the acquired optical property information. Then, the computer 150 displays the image data on the display unit 160. A user can use the image data of the optical property information displayed on the display unit 160 for diagnosis and the like.

Note that in the present embodiment, image data is formed from optical property information and is displayed on the display unit 160, but information to be displayed on the display unit 160 is not limited thereto. For example, a value of optical property information at a specific position may be displayed on the display unit 160. In this case, a user may input a position by using the input unit 170 and a value of optical property information at the input position may be displayed on the display unit 160.

As described, according to the photoacoustic apparatus according to the present embodiment, a component corresponding to a reflected wave of the photoacoustic wave can be reduced from the time-series photoacoustic signal. Thus, optical property information in which decrease in quantitativity due to the component corresponding to the reflected wave of the photoacoustic wave is controlled can be acquired.

Note that the present embodiment can also be applied to a case of reducing a component corresponding to a reflected wave of a photoacoustic wave of a high sound pressure generated by direct emission of light not only to the surface 105 of the subject 100 but also to a member like an acoustic lens.

In the following, each configuration of the photoacoustic apparatus according to the present embodiment will be described.

(Subject 100 and Optical Absorber 101)

These are not what configures a part of the photoacoustic apparatus of the present invention but will be described in the following. The photoacoustic apparatus of the present invention has been made mainly for a diagnosis of a malignant tumor, a blood vessel disease, or the like of a human or an animal, a follow-up of a chemical treatment, or the like. Thus, as a subject, a living body, specifically an object region of diagnosis, such as a breast, a neck, or a stomach of a human body or an animal is assumed.

Also, an optical absorber inside the subject is what having a relatively high absorption coefficient inside the subject. For example, when a human body is a measurement object, a malignant tumor, which includes a great amount of oxy-hemoglobin, deoxyhemoglobin, or methemoglobin or a great number of blood vessels or new blood vessels including a great amount thereof, becomes an object of the optical absorber. In addition, a plaque on a carotid artery wall or the like also becomes the object.

(Light Source 110)

A light source is preferably a pulsed light source which can generate pulsed light of an order of a several nano seconds to a several micro seconds. Specifically, in order to generate a photoacoustic wave effectively, a pulse width around ten nano seconds is used. As the light source, a light emitting diode or the like can be used instead of a laser. As the laser, various lasers such as a solid-state laser, a gas laser, a dye laser, and a semiconductor laser can be used. A wavelength of a light source to be used is preferably a wavelength with which light is propagated inside the subject. Specifically, when the subject is a living body, the wavelength is 500 nm to 1200 nm.

(Optical System 120)

The optical system 120 is a member to lead, to the subject 100, light emitted from a light source while making the light into an intended light distribution shape. The optical system 120 includes an optical part such as a lens or a mirror, an optical waveguide such as an optical fiber, and the like. For example, an optical part is a mirror to reflect light, a lens to collect and increase light and to change a shape thereof, a diffuser panel to diffuse light, or the like. Any kind of optical system 120 can be used as long as the light emitted from the light source is emitted to a subject in an intended shape. Note that it is preferable that light is expanded to an area of a certain degree instead of being collected by a lens in terms of safety to a living body and of a wider diagnosis area. Also, to make it easier to transmit an acoustic wave to an area to which light is emitted, the optical system 120 is configured in such a manner as to light directly below the transducer array 130.

(Transducer Array 130)

As a transducer used for the transducer array 130, any transducer such as what uses a piezoelectric phenomenon, optical resonance, a change in capacitance, or the like can be used as long as an acoustic wave can be transmitted/received.

Note that by including a transmission/reception function of an acoustic wave like the present embodiment, the transducer array 130 can easily receive an acoustic wave in the same area and can easily conserve space, for example. However, functions of an acoustic wave transmission unit, a photoacoustic wave reception unit, and an echo reception unit may be respectively included in different transducer arrays.

(Acoustic Matching Material 140)

The acoustic matching material 140 is not what configures a part of the photoacoustic apparatus of the present invention but will be described. The acoustic matching material 140 is a material provided between the subject 100 and the transducer array 130 to perform acoustic matching of the subject 100 and the transducer array 130. As the acoustic matching material 140, for example, a gel including water, oil, alcohol, or the like is used.

(Computer 150)

As the computer 150, a typical workstation or the like is used. Correction processing, image reconstruction processing, or the like is performed by software programmed in advance. Note that in the present embodiment, various kinds of processing executed by the computer 150 may be different apparatuses.

Also, instead of the software processing performed in a workstation, a property such as acoustic impedance of a subject, or optical property information can be acquired by hardware processing.

A calculation unit 152 in the computer 150 can perform predetermined processing on an electric signal output from the transducer array 130.

The calculation unit 152 typically includes an element such as a CPU, a GPU, or an A/D converter or a circuit such as an FPGA, or an ASIC. Note that the calculation unit 152 does not necessarily include only one element or circuit and may include a plurality of elements or circuits. Also, processing performed by the calculation unit 152 may be executed by any element or circuit.

Also, the calculation unit 152 can control an operation of each configuration of the photoacoustic apparatus. For example, the calculation unit 152 can control time point for emitting pulsed light generated in the light source and can control time point for transmitting/receiving an electric signal with the pulsed light as a trigger signal. By controlling a transmission phase of each transducer in the transducer array 130, the calculation unit 152 can arbitrarily control a wave front of the acoustic wave transmitted by the transducer array 130.

Also, the storage unit 151 in the computer 150 typically includes a storage medium such as a ROM, a RAM, or a hard disk. Note that the storage unit 151 does not necessarily include only one storage medium and may include a plurality of storage media.

Also, it is preferable that the computer 150 can perform pipeline processing of a plurality of signals simultaneously. Accordingly, a period of time before the optical property information is acquired can be reduced.

Note that processing performed by the computer 150 can be stored in the storage unit 151 as a program to be executed by the calculation unit 152. The storage unit 151 into which the program is stored is a non-transitory storage medium.

(Display Unit 160)

The display unit 160 is an apparatus to display optical property information output from a signal processing apparatus. As the display unit 160, any type of display such as a liquid crystal display, a plasma display, an organic electroluminescence display, or an FED can be employed. Note that the display unit 160 may be provided separately from the photoacoustic apparatus of the present invention.

(Input Unit 170)

The input unit 170 is a member with which a user can specify information in order to input the information into the computer 150. As the input unit 170, a keyboard, a mouse, a touch panel, a dial, a button, or the like can be used. When a touch panel is employed as the input unit 170, the display unit 160 may double as the input unit 170.

Second Embodiment

In the second embodiment, echo sound pressure distribution is acquired from a time-series echo signal and initial sound pressure distribution is acquired from a time-series photoacoustic signal. Also, difference distribution between the echo sound pressure distribution and the initial sound pressure distribution is acquired. In the difference distribution acquired in the present embodiment, compared to the initial sound pressure distribution acquired from the time-series photoacoustic signal, a component corresponding to a reflected wave of a photoacoustic wave is reduced. In the following, the present embodiment will be described with reference to an apparatus similar to the photoacoustic apparatus according to the first embodiment.

Figure 4:
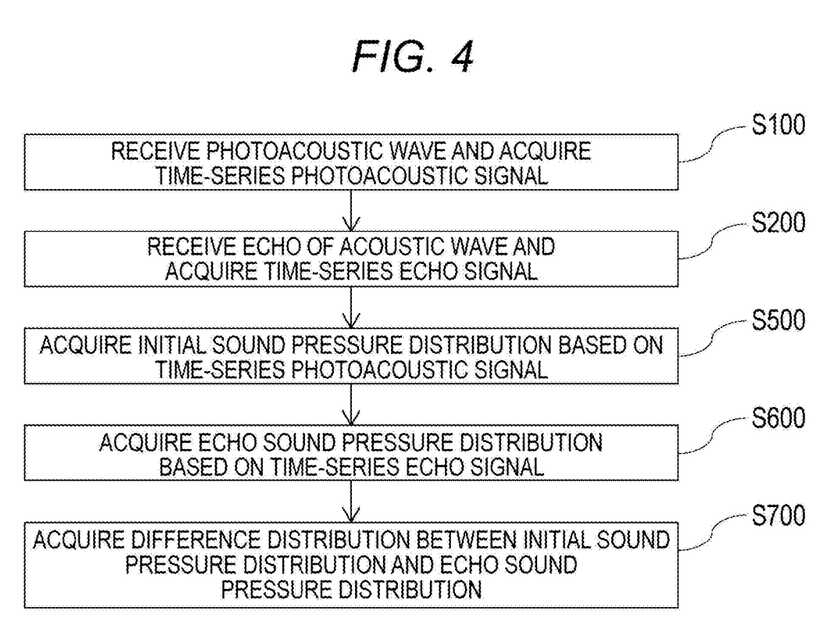
FIG. 4 is a flowchart illustrating an operation flow of a photoacoustic apparatus according to a second embodiment.

An operation method of the photoacoustic apparatus according to the present embodiment will be described with reference to FIG. 4. Note that in a flow illustrated in FIG. 4, in respect to processing similar to the processing illustrated in FIG. 2, the same reference sign is assigned and detail description will not be repeated.

First, in the present embodiment, processes S100 and S200 are performed and a time-series photoacoustic signal S1 (t) and a time-series echo signal S2 (t) are acquired.

(S500: Process for Acquiring Initial Sound Pressure Distribution Based on Time-Series Photoacoustic Signal)

Subsequently, based on the time-series photoacoustic signal S1 (t), a computer 150 acquires initial sound pressure distribution P1 (r) which is an example of optical property information. Here, the computer 150 acquires the initial sound pressure distribution P1 (r) from the time-series photoacoustic signal S1 (t) by a method for acquiring optical property information from a difference signal S3 (t), the method being described in S400.

Figure 5A:
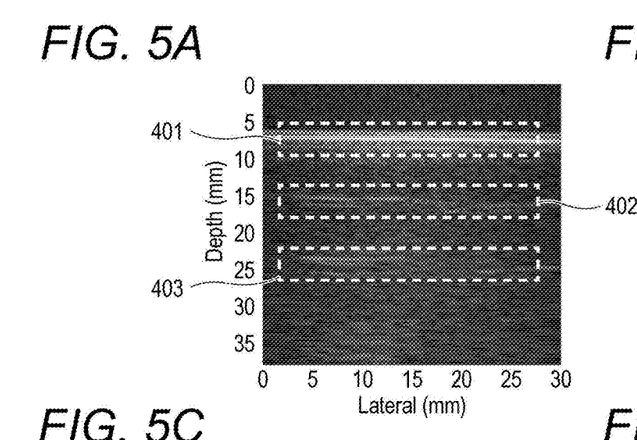
FIGS. 5A to 5D are views illustrating various kind of distribution which can be acquired in the second embodiment.

FIG. 5A is a view illustrating an example of the initial sound pressure distribution P1 (r) acquired from the time-series photoacoustic signal S1 (t). A vertical axis indicates a depth of a subject 100 and the depth of the subject 100 becomes larger in a downward direction. Note that in the present embodiment, light is emitted from an upside of the drawing and a photoacoustic wave is received in the upside of the drawing.

An area with high contrast (white area) which is in a shallow position in FIG. 5A illustrates initial sound pressure distribution 401 indicating a surface 105 of the subject 100 to which light is directly emitted, and in a deep part thereof, initial sound pressure distribution 402 indicating an optical absorber 101 is illustrated. In a further deeper part, initial sound pressure distribution 403 indicating a virtual image formed from a received signal of a reflected wave 104c is illustrated.

(S600: Process for Acquiring Echo Sound Pressure Distribution Based on Time-Series Echo Signal)

Subsequently, the computer 150 acquires echo sound pressure distribution P2 (r) based on the time-series echo signal S2 (t).

The computer 150 according to the present embodiment acquires the echo sound pressure distribution P2 (r) in such a manner that a position of the initial sound pressure distribution 403 indicating a virtual image in FIG. 5A and a position of the echo sound pressure distribution P2 (r) acquired from the time-series echo signal S2 (t) become identical. That is, by using an echo signal corresponding to reception time of a photoacoustic signal used to acquire an initial sound pressure in a specific minimum unit, an echo sound pressure in a specific minimum unit is acquired. For example, the computer 150 acquires the echo sound pressure distribution P2 (r) from the time-series echo signal S2 (t) on the assumption that an echo is generated in the subject 100 simultaneously when an acoustic wave 102a reaches the surface 105 of the subject 100. That is, in consideration of propagation time from time when the acoustic wave 102a reaches the surface 105 of the subject 100 to time when an echo reaches a transducer array 130, the echo sound pressure in each minimum unit is acquired from the time-series echo signal. Accordingly, it is possible to make a coordinate in the initial sound pressure distribution P1 (r), at which coordinate an initial sound pressure corresponding to a reflected wave 104b appears, and a coordinate in the echo sound pressure distribution P2 (r), at which coordinate an echo sound pressure corresponding to an echo 102b appears, identical.

On the other hand, generally, in a case of acquiring a B mode image from a time-series echo signal, the B mode image is acquired in consideration of propagation time in each minimum unit of when transmission/reception is performed between the transducer array 130 and a position in a minimum unit to be imaged. However, the B mode image acquired by this method and the initial sound pressure distribution 403 indicating a virtual image in FIG. 5A are not identical, and thus, even when a difference therebetween is acquired, there is not much effect to reduce a reflected wave component of the time-series photoacoustic signal.

Figure 5B:
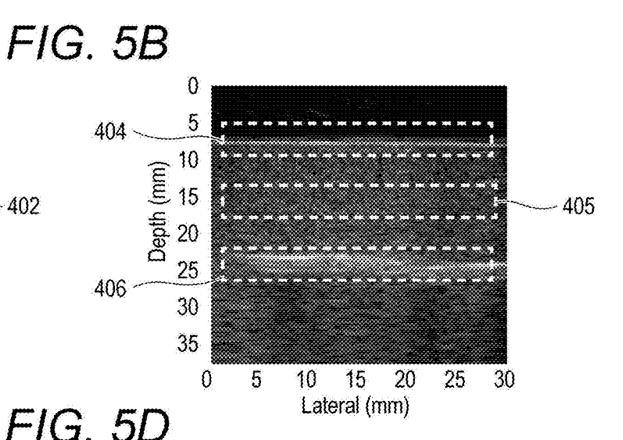

FIG. 5B is a view illustrating the echo sound pressure distribution P2 (r) acquired from the time-series echo signal S2 (t) by a method corresponding to the present embodiment. An area with high contrast (white area) in a shallow position of FIG. 5B is echo sound pressure distribution 404 indicating the surface 105 of the subject 100, and in a deep part thereof, echo sound pressure distribution 406 indicating the optical absorber 101 is illustrated. Note that in the present embodiment, an acoustic wave is transmitted from an upside in the drawing and an echo is received in the upside in the drawing.

When FIGS. 5A and 5B are compared, it can be understood that the initial sound pressure distribution 403 indicating the virtual image in FIG. 5A and the echo sound pressure distribution 406 indicating the optical absorber 101 in FIG. 5B are identical. On the other hand, strong echo sound pressure distribution is not seen in an area 405 in which the initial sound pressure distribution 402 indicating the optical absorber 101 has appeared in FIG. 5A. That is, in the area 405, there is no echo sound pressure distribution which is identical to the initial sound pressure distribution 402 indicating the optical absorber 101.

Figure 5C:
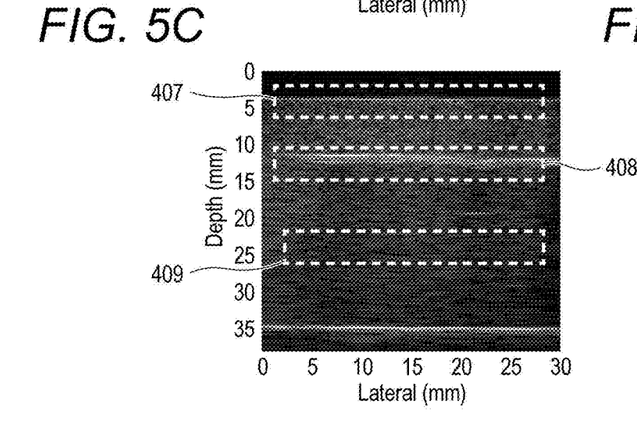

On the other hand, a B mode image acquired from the time-series echo signal S2 (t) by a general acquiring method of a B mode image is illustrated in FIG. 5C as a comparison example. An area with high contrast (white area) in a shallow position in FIG. 5C is a B mode image 407 indicating the surface 105 of the subject 100 and in a deep part thereof, a B mode image 408 indicating the optical absorber 101 is illustrated.

When FIGS. 5A and 5C are compared, in an area 409 in which the initial sound pressure distribution 403 indicating the virtual image has appeared in FIG. 5A, no B mode image is seen. That is, in the area 409, there is not a B mode image identical to the initial sound pressure distribution 403 indicating the virtual image.

(S700: Process for Acquiring Differential Sound Voltage Distribution Between Initial Sound Pressure Distribution and Echo Sound Pressure Distribution)

Subsequently, the computer 150 acquires difference distribution P3 (r) between the initial sound pressure distribution P1 (r) acquired in S500 and the echo sound pressure distribution P2 (r) acquired in S600.

<Weighting>

Incidentally, there is a case where intensity of the photoacoustic wave 104b generated on the surface 105 of the subject 100 and that of the acoustic wave 102a transmitted from the transducer array 130 are different from each other. In such a case, it is preferable that a difference between the initial sound pressure distribution and the echo sound pressure distribution is calculated and the difference distribution P3 (r) is acquired after weighting is performed on the initial sound pressure distribution P1 (r) or the echo sound pressure distribution P2 (r). By performing such weighting processing, a component corresponding to a reflected wave in the initial sound pressure distribution P1 (r) can be greatly reduced.

The following equation is an equation expressing an example of the described weighting processing.

$$P3(r) = P1(r) - A \times P2(r) \quad (2)$$

Here, A is a weighting coefficient. The weighting coefficient A can be arbitrarily set by a user or a computer to reduce a difference between an initial sound pressure value corresponding to a reflected wave generated due to reflection of a photoacoustic wave by a reflector and an echo sound pressure value at the same position.

For example, a user specifies an arbitrary area with the input unit 170 in respect to the initial sound pressure distribution P1 (r) or the echo sound pressure distribution P2 (r) displayed on the display unit 160. Subsequently, the computer 150 can set, as the weighting coefficient A, a value with which a difference between the initial sound pressure and the echo sound pressure in the area specified by the user becomes small. Also, the computer 150 can set, as the weighting coefficient A, a value with which a difference between an average initial sound pressure value in the specified area and an average echo sound pressure value in the specified area becomes small.

Also, it may be possible for a user to set, with the input unit 170, a weighting coefficient while checking the difference distribution displayed on the display unit 160. Thus, the display unit 160 preferably includes the input unit 170 with which a weighting coefficient can be input. For example, the display unit 160 may be a touch panel which doubles as the input unit 170.

Note that in an example of the weighting expressed in the equation 2, the weighting is performed by multiplying the echo sound pressure distribution P2 (r) by a weighting coefficient. Note that in the present embodiment, the weighting may be performed by multiplying the initial sound pressure distribution P1 (r) by a weighting coefficient or the weighting may be performed by multiplying both of the initial sound pressure distribution P1 (r) and echo sound pressure distribution P2 (r) by a weighting coefficient. However, to maintain quantitativity of optical property information acquired from the initial sound pressure distribution P1 (r), only the echo sound pressure distribution P2 (r) is preferably multiplied by a weighting coefficient.

Figure 5D:
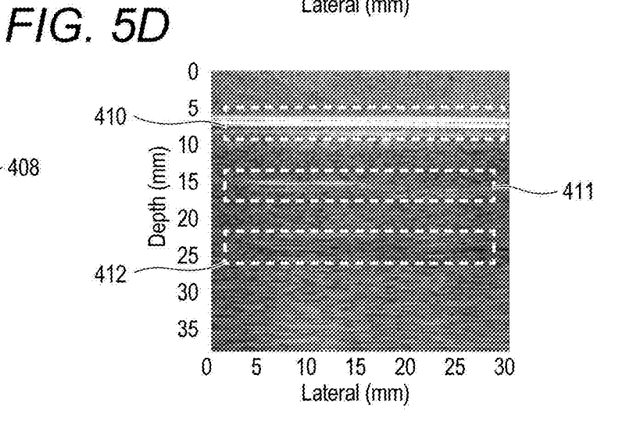

In the present embodiment, the echo sound pressure distribution P2 (r) is multiplied by the weighting coefficient a=0.4 and the difference distribution P3 (r) is acquired. An example of difference distribution acquired as a result of such processing is illustrated in FIG. 5D. In FIG. 5D, difference distribution 410 indicating the surface 105 of the subject 100, difference distribution 411 indicating the optical absorber 101, and an area 412 in which a virtual image has appeared in FIG. 5A are illustrated. As it can be seen from FIG. 5D, the initial sound pressure distribution 413 indicating the virtual image is reduced in the area 412 and cannot be seen. On the other hand, the optical absorber 101 is not reduced greatly and can be seen as the difference distribution 411. That is, according to the present embodiment, initial sound pressure distribution indicating a virtual image, which is by a reflected wave component of the photoacoustic wave, can be reduced selectively.

<Deviation Correction of Reception Time>

Incidentally, when signals do not appear at the same time due to positional deviation or the like of a subject, an effect to reduce a component corresponding to a reflected wave of the photoacoustic wave may be deteriorated in a method described in the first embodiment. Thus, in the second embodiment, the initial sound pressure distribution and the echo sound pressure distribution may be acquired in a minimum unit larger than a product of reception sampling time and a speed of sound in the subject. That is, an initial sound pressure and an echo sound pressure in a certain minimum unit may be acquired from a plurality of pieces of sampling data. Accordingly, components corresponding to a photoacoustic wave and an echo, which are generated by the same reflector respectively in an initial sound pressure and an echo sound pressure in a certain minimum unit, become more likely to be included. Thus, even when a reflected wave of the photoacoustic wave and an echo do not appear at the same time, a component corresponding to the reflected wave of the photoacoustic wave can be reduced by acquiring difference distribution between the initial sound pressure distribution and the echo sound pressure distribution. Note that when reception sampling time of the photoacoustic signal and that of the echo signal are different from each other, it is preferable to acquire the initial sound pressure distribution and the echo sound pressure distribution by a product of longer reception sampling time and a speed of sound in the subject.

Note that the computer 150 acquires light quantity distribution, of light emitted to the subject 100 in S100, in the subject 100 and corrects difference distribution by the light quantity distribution, and thus, absorption coefficient distribution as optical property information can be acquired. Also, by using light of a plurality of wavelengths, the computer 150 can acquire absorption coefficient distribution corresponding to each wavelength. By using the absorption coefficient distribution, the computer 150 can acquire, as the optical property information, a concentration of a substance included in the subject 100.

As described, in the difference distribution acquired in the present embodiment, a component corresponding to a reflected wave of the photoacoustic wave is reduced compared to the initial sound pressure distribution acquired from the time-series photoacoustic signal. That is, according to the photoacoustic apparatus according to the present embodiment, optical property information, in which decrease in quantitativity due to a component corresponding to a reflected wave of the photoacoustic wave is controlled, can be acquired.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-209624, filed 2013 Oct. 4, which is hereby incorporated by reference herein in its entirety.

What is claimed is:

1. A photoacoustic apparatus comprising:
a light irradiating unit configured to irradiate light onto a subject;
an acoustic wave transmission unit configured to transmit an acoustic wave to a specific area within the subject;
a photoacoustic wave reception unit configured to receive a photoacoustic wave generated by irradiation of the light to an area of the subject including the specific area and configured to output a photoacoustic signal;
an echo reception unit configured to receive, at a timing different from that of reception of the photoacoustic wave, an echo generated due to reflection of the acoustic wave transmitted from the acoustic wave transmission unit and configured to output an echo signal; and
a processing unit configured to acquire, based on the photoacoustic signal and the echo signal, optical property information in which a component corresponding to a reflected wave of the photoacoustic wave generated in the specific area is reduced.

2. The photoacoustic apparatus according to claim 1, wherein the processing unit acquires a difference signal which represents a difference between the photoacoustic signal and the echo signal and acquires the optical property information by using the difference signal.

3. The photoacoustic apparatus according to claim 2, wherein the processing unit acquires the difference signal after performing weighting, with a weighting coefficient, on at least one of the photoacoustic signal and the echo signal.

4. The photoacoustic apparatus according to claim 3, wherein the processing unit acquires a correlation between the photoacoustic signal and the echo signal and sets the weighting coefficient with which a difference between amplitude of the photoacoustic signal and that of the echo signal, which signals have a high correlation with each other, becomes small.

5. The photoacoustic apparatus according to claim 4, wherein the processing unit acquires the difference signal after performing weighting, with the weighting coefficient, only on the echo signal.

6. The photoacoustic apparatus according to claim 3, wherein the processing unit acquires the difference signal after performing weighting, with the weighting coefficient, only on the echo signal.

7. The photoacoustic apparatus according to claim 1, wherein the processing unit acquires a difference signal after correcting at least one of the photoacoustic signal and the echo signal in such a manner that a difference between reception time of a photoacoustic signal corresponding to a reflected wave generated due to reflection of the photoacoustic wave by a specific reflector and reception time of an echo signal corresponding to an echo generated due to reflection of the transmitted acoustic wave by the specific reflector becomes small.

8. The photoacoustic apparatus according to claim 1, wherein the processing unit acquires a correlation between the photoacoustic signal and the echo signal and acquires a difference signal after correcting at least one of the photoacoustic signal and the echo signal in such a manner that a difference between reception time of the photoacoustic signal and that of the echo signal, which signals have a high correlation with each other, becomes small.

9. The photoacoustic apparatus according to claim 1, wherein the processing unit deletes, from the echo signal, an echo signal acquired in a period of time in which the acoustic wave is propagated from the acoustic wave transmission unit to the certain area.

10. The photoacoustic apparatus according to claim 1, wherein the processing unit starts acquiring an echo signal at a time point at which the acoustic wave is propagated from the acoustic wave transmission unit to the specific area.

11. The photoacoustic apparatus according to claim 1, wherein the processing unit acquires initial sound pressure distribution based on the photoacoustic signal, acquires echo sound pressure distribution based on the echo signal, and acquires difference distribution between the initial sound pressure distribution and the echo sound pressure distribution.

12. The photoacoustic apparatus according to claim 11, wherein the processing unit acquires the difference distribution after performing weighting, with a weighting coefficient, on at least one of the initial sound pressure distribution and the echo sound pressure distribution.

13. The photoacoustic apparatus according to claim 12, wherein the processing unit sets the weighting coefficient with which a difference between an initial sound pressure value and an echo sound pressure value in an arbitrary area becomes small.

14. The photoacoustic apparatus according to claim 13, further comprising an input unit with which a user can specify the arbitrary area from the initial sound pressure distribution or the echo sound pressure distribution displayed on a display unit.

15. The photoacoustic apparatus according to claim 12, wherein the processing unit acquires the difference distribution after performing weighting, with the weighting coefficient, only on the echo sound pressure distribution.

16. The photoacoustic apparatus according to claim 11, wherein the photoacoustic wave reception unit and the echo reception unit respectively receive the photoacoustic signal and the echo signal at the same reception sampling time, and
the processing unit acquires the initial sound pressure distribution and the echo sound pressure distribution in a minimum unit larger than a product of the reception sampling time and a speed of sound.

17. The photoacoustic apparatus according to claim 11, wherein the photoacoustic wave reception unit and the echo reception unit respectively acquire the photoacoustic signal and the echo signal at different reception sampling time, and the processing unit acquires the initial sound pressure distribution and the echo sound pressure distribution in a minimum unit larger than a product of longer reception sampling time in the different reception sampling time and a speed of sound.

18. A photoacoustic apparatus comprising:

a light irradiating unit configured to irradiate light onto a subject;

an acoustic wave transmission unit configured to transmit an acoustic wave;

a photoacoustic wave reception unit configured to receive a photoacoustic wave generated by irradiation of the light to the subject and configured to output a photoacoustic signal;

an echo reception unit configured to receive, at a timing different from that of reception of the photoacoustic wave, an echo generated due to reflection of the acoustic wave transmitted from the acoustic wave transmission unit and configured to output an echo signal; and a processing unit configured to acquire a difference signal which represents a difference between the photoacoustic signal and the echo signal and further configured to acquire optical property information by using the difference signal.

19. A photoacoustic apparatus comprising:

a light irradiation configured to irradiate light onto a subject;

an acoustic wave transmission unit configured to transmit an acoustic wave;

a photoacoustic wave reception unit configured to receive a photoacoustic wave generated by irradiation of the light to the subject and configured to output a photoacoustic signal;

an echo reception unit configured to receive, at a timing different from that of reception of the photoacoustic wave, an echo generated due to reflection of the acoustic wave transmitted from the acoustic wave transmission unit and configured to output an echo signal; and a processing unit configured to acquire initial sound pressure distribution based on the photoacoustic signal, acquire echo sound pressure distribution based on the echo signal, and acquire difference distribution between the initial sound pressure distribution and the echo sound pressure distribution.

* * * * *